United States Patent
Choi et al.

(10) Patent No.: US 9,675,303 B2
(45) Date of Patent: Jun. 13, 2017

(54) VISUALIZATION SYSTEMS, INSTRUMENTS AND METHODS OF USING THE SAME IN SPINAL DECOMPRESSION PROCEDURES

(71) Applicant: VertiFlex, Inc., San Clemente, CA (US)

(72) Inventors: Andy W. Choi, Irvine, CA (US); Thomas R. Haley, Lafayette Hill, PA (US); Scott C. Lynch, San Clemente, CA (US)

(73) Assignee: VertiFlex, Inc., Carlsbad, CA (US)

( * ) Notice: Subject to any disclaimer, the term of this patent is extended or adjusted under 35 U.S.C. 154(b) by 711 days.

(21) Appl. No.: 13/844,324

(22) Filed: Mar. 15, 2013

(65) Prior Publication Data

US 2014/0275992 A1    Sep. 18, 2014

(51) Int. Cl.
*A61B 5/05* (2006.01)
*A61B 6/12* (2006.01)
(Continued)

(52) U.S. Cl.
CPC .............. *A61B 6/12* (2013.01); *A61B 6/487* (2013.01); *A61B 17/1671* (2013.01); *A61B 17/320016* (2013.01); *A61B 17/1659* (2013.01); *A61B 17/32002* (2013.01); *A61B 17/3401* (2013.01); *A61B 17/3421* (2013.01); *A61B 90/361* (2016.02); *A61B 2017/0256* (2013.01); *A61B 2017/320048* (2013.01); *A61B 2090/08021* (2016.02)

(58) Field of Classification Search
CPC ....... A61B 6/12; A61B 17/16; A61B 17/1671; A61B 17/320016; A61B 19/00; A61B 6/487; A61B 17/1659; A61B 2017/320048; A61B 2019/481; A61B 19/5212; A61B 17/3421; A61B 17/3401; A61B 2017/0256
See application file for complete search history.

(56) References Cited

U.S. PATENT DOCUMENTS

| | | |
|---|---|---|
| 2,248,054 A | 7/1941 | Becker |
| 2,677,369 A | 5/1954 | Knowles |

(Continued)

FOREIGN PATENT DOCUMENTS

| | | |
|---|---|---|
| CA | 268461 A | 2/1927 |
| CN | 2794456 Y | 7/2006 |

(Continued)

OTHER PUBLICATIONS

International Search Report, counterpart PCT Application PCT/US2013/038534, Aug. 7, 2013, 16 pages.

(Continued)

*Primary Examiner* — Jonathan Cwern
(74) *Attorney, Agent, or Firm* — Perkins Coie LLP

(57) ABSTRACT

A method for positioning a treatment instrument in a subject involves positioning a tissue protector of a visualization instrument in an epidural space of the subject. The tissue protector is viewed and positioned in the epidural space using fluoroscopy. A treatment instrument between a first vertebra and a second vertebra and while viewing the tissue protector positioned in the epidural space. A decompression procedure is performed using the treatment instrument.

20 Claims, 8 Drawing Sheets

(51) Int. Cl.
*A61B 6/00* (2006.01)
*A61B 17/16* (2006.01)
*A61B 17/32* (2006.01)
*A61B 17/34* (2006.01)
*A61B 17/02* (2006.01)
*A61B 90/00* (2016.01)

(56) References Cited

U.S. PATENT DOCUMENTS

| | | |
|---|---|---|
| 3,242,120 A | 3/1966 | Steuber |
| 3,486,505 A | 12/1969 | Morrison |
| 3,648,691 A | 3/1972 | Lumb et al. |
| 3,986,383 A | 10/1976 | Petteys |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 † | 8/2003 | Sharps |
| 6,610,065 B1 | 8/2003 | Branch et al. |
| 6,610,091 B1 | 8/2003 | Reiley |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 † | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |

(56) References Cited

U.S. PATENT DOCUMENTS

| | | |
|---|---|---|
| 6,783,529 B2 | 8/2004 | Hover et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |

(56) References Cited

U.S. PATENT DOCUMENTS

| | | |
|---|---|---|
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 2001/0031965 A1 | 10/2001 | Zucherman et al. |
| 2002/0042607 A1 | 4/2002 | Palmer et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0261768 A1 | 11/2005 | Trieu |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |

(56) References Cited

U.S. PATENT DOCUMENTS

| | | |
|---|---|---|
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1† | 11/2007 | Solsberg |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1* | 7/2008 | Perez-Cruet ....... A61B 17/7065 606/249 |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0287997 A1* | 11/2008 | Altarac .............. A61B 17/7065 606/249 |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1* | 5/2010 | Mehdizade ........ A61B 17/3421 606/87 |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0228884 A1 | 8/2014 | Altarac et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2015/0374415 A1 | 12/2015 | Kim |
| 2016/0030092 A1 | 2/2016 | Altarac et al. |
| 2016/0045232 A1 | 2/2016 | Altarac et al. |
| 2016/0066963 A1 | 3/2016 | Kim |
| 2016/0135853 A1 | 5/2016 | Altarac et al. |
| 2016/0248222 A1 | 8/2016 | Miyata |
| 2016/0317193 A1 | 11/2016 | Kim et al. |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |

(56) References Cited

FOREIGN PATENT DOCUMENTS

| | | |
|---|---|---|
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-2004073533 A1 | 9/2004 |
| WO | WO-2004110300 A2 | 12/2004 |
| WO | WO-2005009300 A1 | 2/2005 |
| WO | WO-2005013839 A2 | 2/2005 |
| WO | WO-2005025461 A2 | 3/2005 |
| WO | WO-2005041799 A1 | 5/2005 |
| WO | WO-2005044152 A1 | 5/2005 |
| WO | WO-2005055868 A2 | 6/2005 |
| WO | WO-2005079672 A2 | 9/2005 |
| WO | WO-2005086776 A2 | 9/2005 |
| WO | WO-2005115261 A1 | 12/2005 |
| WO | WO-2006033659 A2 | 3/2006 |
| WO | WO-2006034423 A2 | 3/2006 |
| WO | WO-2006039243 | 4/2006 |
| WO | WO-2006039260 A2 | 4/2006 |
| WO | WO-2006045094 A2 | 4/2006 |
| WO | WO-2006063047 A2 | 6/2006 |
| WO | WO-2006064356 A1 | 6/2006 |
| WO | WO-2006065774 A1 | 6/2006 |
| WO | WO-2006089085 A2 | 8/2006 |
| WO | WO-2006102269 A2 | 9/2006 |
| WO | WO-2006102428 A1 | 9/2006 |
| WO | WO-2006102485 A2 | 9/2006 |
| WO | WO-2006107539 A1 | 10/2006 |
| WO | WO-2006110462 A2 | 10/2006 |
| WO | WO-2006110464 A1 | 10/2006 |
| WO | WO-2006110767 A1 | 10/2006 |
| WO | WO-2006113080 A2 | 10/2006 |
| WO | WO-2006113406 A2 | 10/2006 |
| WO | WO-2006113814 A2 | 10/2006 |
| WO | WO-2006118945 A1 | 11/2006 |
| WO | WO-2006119235 A1 | 11/2006 |
| WO | WO-2006119236 A2 | 11/2006 |
| WO | WO-2006135511 A1 | 12/2006 |
| WO | WO-2007015028 A1 | 2/2007 |
| WO | WO-2007035120 A1 | 3/2007 |
| WO | WO-2007075375 A2 | 7/2007 |
| WO | WO-2007075788 A2 | 7/2007 |
| WO | WO-2007075791 A2 | 7/2007 |
| WO | WO-2007089605 A2 | 8/2007 |
| WO | WO-2007089905 A2 | 8/2007 |
| WO | WO-2007089975 A1 | 8/2007 |
| WO | WO-2007097735 A2 | 8/2007 |
| WO | WO-2007109402 A2 | 9/2007 |
| WO | WO-2007110604 A1 | 10/2007 |
| WO | WO-2007111795 A1 | 10/2007 |
| WO | WO-2007111979 A2 | 10/2007 |
| WO | WO-2007111999 A2 | 10/2007 |
| WO | WO-2007117882 A1 | 10/2007 |
| WO | WO-2007121070 A2 | 10/2007 |
| WO | WO-2007127550 A2 | 11/2007 |
| WO | WO-2007127588 A1 | 11/2007 |
| WO | WO-2007127677 A1 | 11/2007 |
| WO | WO-2007127689 A2 | 11/2007 |
| WO | WO-2007127694 A2 | 11/2007 |
| WO | WO-2007127734 A2 | 11/2007 |
| WO | WO-2007127736 A2 | 11/2007 |
| WO | WO-2007131165 A2 | 11/2007 |
| WO | WO-2007134113 A2 | 11/2007 |
| WO | WO-2008009049 A1 | 1/2008 |
| WO | WO-2008048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

McCulloch, John A., Young, Paul H., "Essentials of Spinal Microsurgery," 1998, pp. 453-485. Lippincott-Raven Publishers, Philadelphia, PA (37 pages total).

Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).

Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).

Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).

Vertos mild Devices Kit—PRT-00430-C—Instructions for Use (13 pages total); see http://vertosmed.com/docs/mildIFU_PRT-00430-C.pdf.

Decision on Petition in U.S. Appl. No. 60/592,099, May 4, 2005.

Vaccaro, Alexander J. et al., MasterCases Spine Surgery, 2001, pp. 100-107. Thieme Medical Publishers, Inc., NY. (10 pages total).

Tredway, Trent L. et al., "Minimally Invasive Transforaminal Lumbar Interbody Fusion (MI-TLIF) and Lateral Mass Fusion with the MetRx System." (14 pages total).

Fast, Avital et al., "Surgical Treatment of Lumbar Spinal Stenosis in the Elderly," Arch Phys. Med Rehabil., Mar. 1985, pp. 149-151, vol. 66.

Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.

International Search Report and Written Opinion; Application No. PCT/US2005/044256; Mailing Date: Jul. 28, 2006, 7 pages.

International Search Report and Written Opinion; Application No. PCT/US2006/047824; Mailing Date: Oct. 16, 2008, 17 pages.

International Search Report and Written Opinion; Application No. PCT/US2006/048611; Mailing Date: Oct. 14, 2008; 10 pages.

International Search Report and Written Opinion; Application No. PCT/US2006/048614; Mailing Date: Feb. 3, 2006; 23 pages.

International Search Report and Written Opinion; Application No. PCT/US2007/022171; Mailing Date: Apr. 15, 2008, 9 pages.

International Search Report and Written Opinion; Application No. PCT/US2007/023312; Mailing Date: May 22, 2008, 14 pages.

International Search Report and Written Opinion; Application No. PCT/US2008/004901; Mailing Date: Aug. 19, 2008, 7 pages.

International Search Report and Written Opinion; Application No. PCT/US2008/008382; Mailing Date: Mar. 2, 2009, 13 pages.

(56) References Cited

OTHER PUBLICATIONS

International Search Report and Written Opinion; Application No. PCT/US2008/008983; Mailing Date: Feb. 23, 2009, 7 pages.
International Search Report and Written Opinion; Application No. PCT/US2008/075487; Mailing Date: Dec. 31, 2008, 7 pages.
International Search Report and Written Opinion; Application No. PCT/US2008/087527; Mailing Date: Jul. 30, 2009, 10 pages.
International Search Report and Written Opinion; Application No. PCT/US2009/031150; Mailing Date: Aug. 28, 2009, 6 pages.
International Search Report and Written Opinion; Application No. PCT/US2009/036561; Mailing Date: Sep. 17, 2009, 12 pages.
Minns, R.J., et al., "Preliminary Design and Experimental Studies of a Noval Soft Implant for Correcting Sagittal Plane Instability in the Lumbar Spine," (1997) Spine, 22(16): 1819-1827.
Swan, Colby, "Preliminary Design and Experimental Studies of a Novel Soft Implant for Correcting Sogittal Plane Instability in the Lumbar Spine," Spine, 1997, 22(16), 1826-1827.
International Search Report and Written Opinion; Application No. PCT/US2010/060498; Mailing Date: Aug. 25, 2011, 17 pages.
International Search Report and Written Opinion; Application No. PCT/US2009/029537; Applicant: Vertiflex, Inc. Mailing Date: Aug. 3, 2015, 14 pages.
European Extended Search Report Application No. EP13780608.9; Applicant: VertiFlex, Inc.; Date of Mailing: Nov. 23, 2015, 8 pages.
ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
Australia Exam Report for Application No. AU2014203394, Applicant: VertiFlex, Inc., Date of Issue: Mar. 15, 2016, 2 pages.
Australia Exam Report for Application No. AU2014203394, Applicant: VertiFlex, Inc.; Date of Issue: Mar. 15, 2016, 2 pages.
Chinese Office Action for Application No. 201380027796.3; Applicant: VertiFlex, Inc.; Date of Mailing: Jun. 1, 2016, 12 pages.
European Further Exam Report for Application No. EP09702116.6; Applicant: VertiFlex, Inc.; Date of Mailing: Jul. 4, 2016, 4 pages.
European Search Report Application No. EP05815519.3; Applicant: The Board of Trustees of the Leland Stanford Junior University; Date of Mailing: Mar. 2, 2016, 4 pages.

\* cited by examiner
† cited by third party

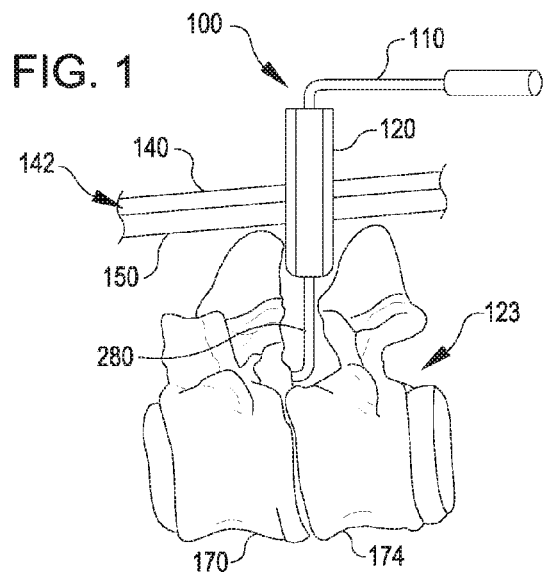
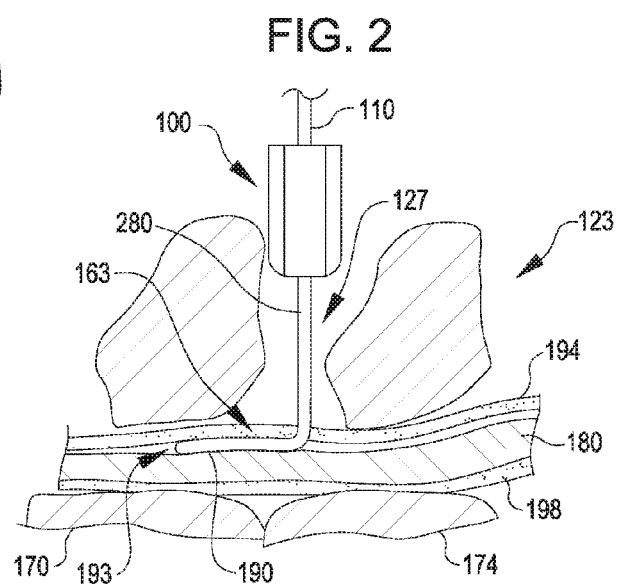
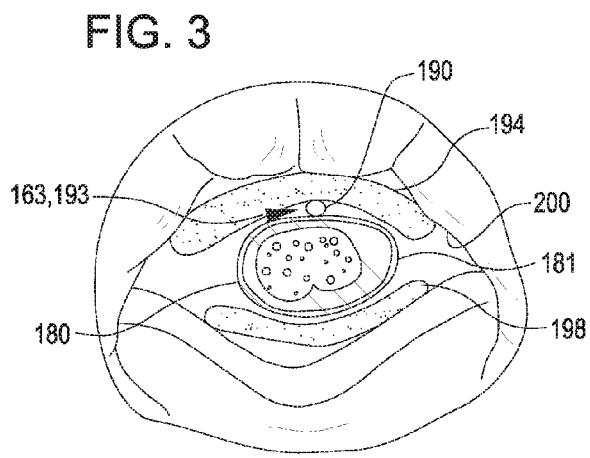

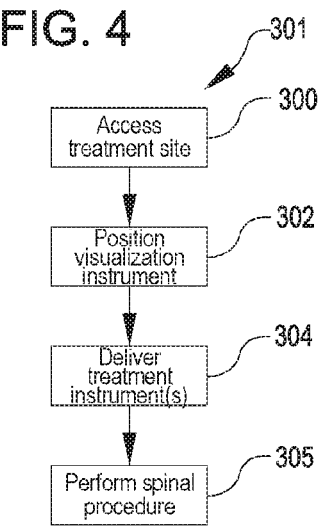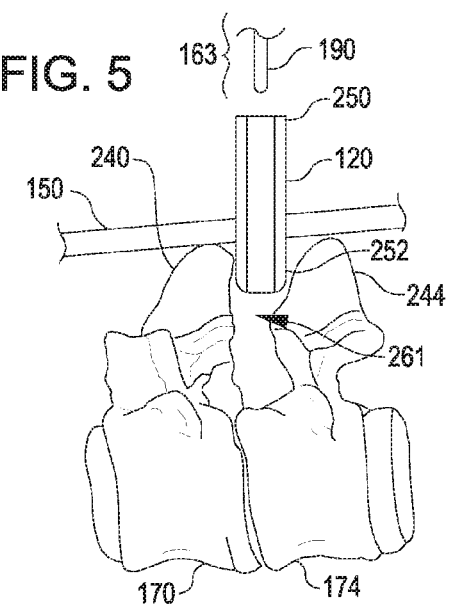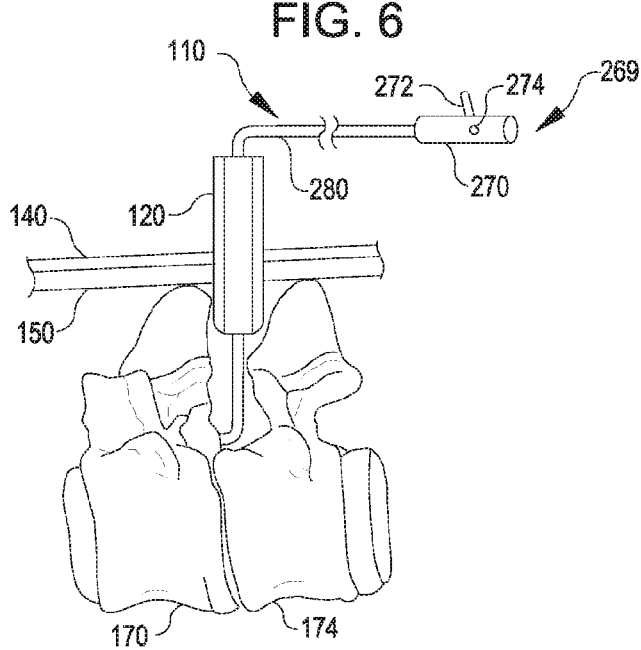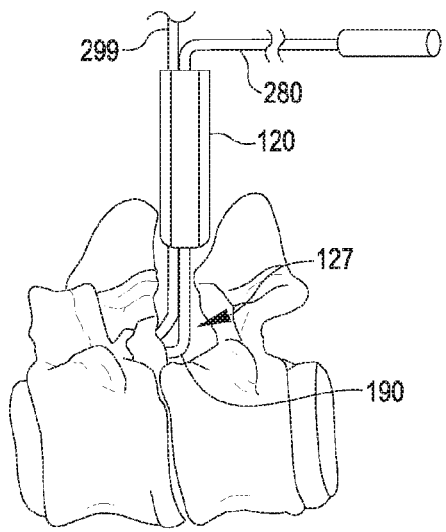

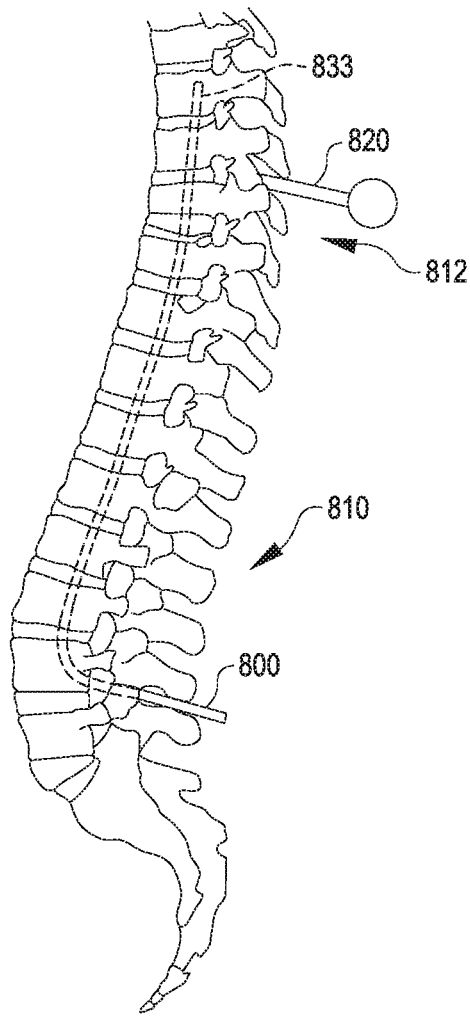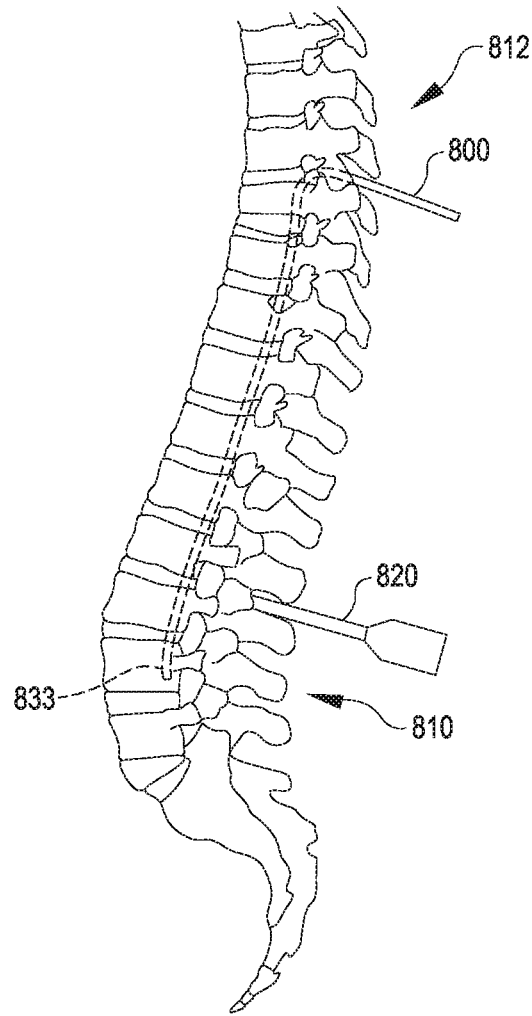

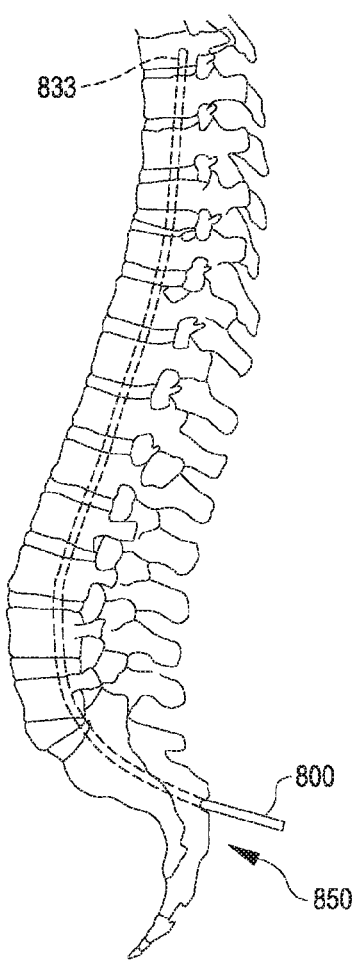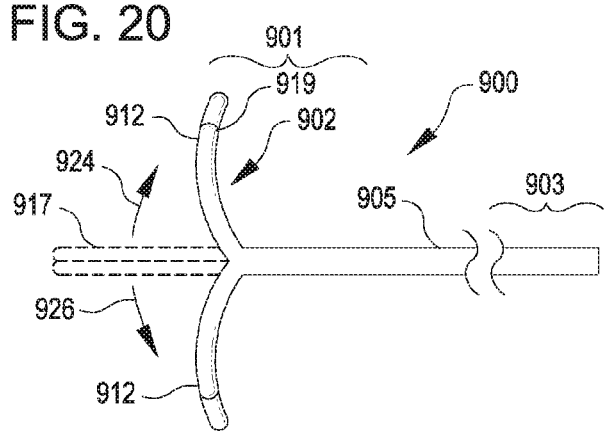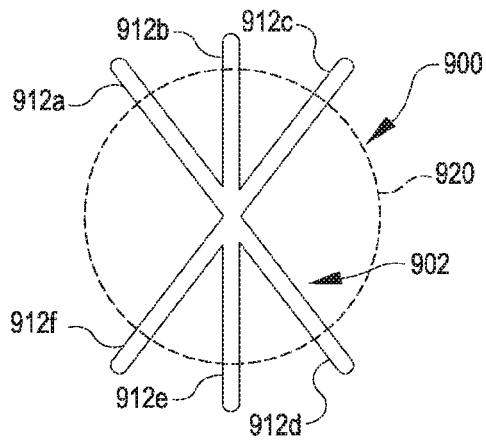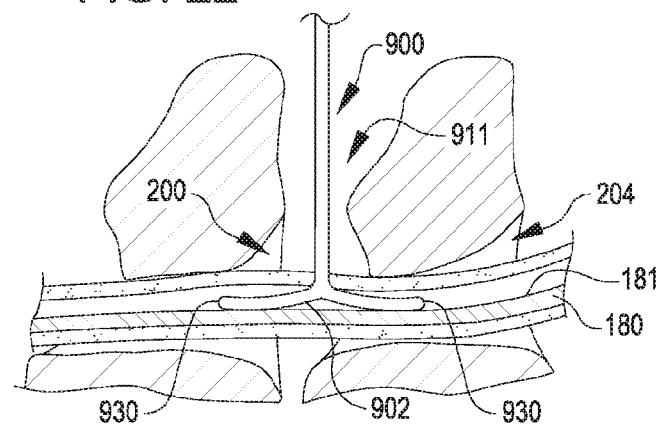

VISUALIZATION SYSTEMS, INSTRUMENTS AND METHODS OF USING THE SAME IN SPINAL DECOMPRESSION PROCEDURES

TECHNICAL FIELD

The present disclosure relates generally to medical systems and, more particularly, to visualization systems, treatment systems, and methods for treating the spine.

BACKGROUND

Spinal nerve compression can be caused by narrowing of the spinal canal associated with arthritis (e.g., osteoarthritis) of the spine, degeneration of spinal discs, and thickening of ligaments. Arthritis of the spine often leads to the formation of bone spurs which can narrow the spinal canal and press on the spinal cord. In spinal disk degeneration, inner tissue of the disk can protrude through a weakened fibrous outer covering of the disk. The bulging inner tissue can press on the spinal cord and/or spinal nerve roots. Ligaments located along the spine can thicken over time and press on the spinal cord and/or or nerve roots. Spinal nerve compression can cause lower back pain, hip pain, and leg pain and may also result in numbness, depending on the location of the compressed nerve tissue. In the lower back, spinal stenosis may lead to spinal cord compression and numbness of the legs. Unfortunately, it may be difficult to treat spinal nerve compression without injuring or traumatizing non-targeted tissue.

BRIEF DESCRIPTION OF THE DRAWINGS

The same reference numerals refer to like parts or acts throughout the various views, unless otherwise specified.

FIG. 1 is a side view of a visualization system in accordance with an embodiment of the disclosure.

FIG. 2 is a side view of a visualization instrument protecting a spinal cord in accordance with an embodiment of the disclosure.

FIG. 3 is an enlarged superior view of tissue adjacent to a vertebral foramen and the visualization instrument positioned between a ligamentum flavum and dura sac.

FIG. 4 is a flowchart illustrating a method for reducing spinal nerve compression in accordance with one embodiment of the disclosure.

FIGS. 5-8 illustrate various stages of a procedure for reducing spinal nerve compression in accordance with one embodiment of the disclosure.

FIGS. 17-19 are side views of a visualization instrument and treatment system positioned along a spine.

FIG. 20 is a side view of the visualization instrument in accordance with an embodiment of the disclosure.

FIG. 21 is a plan view of the visualization instrument of FIG. 20.

FIG. 22 is a side view of a distal portion of the visualization instrument of FIG. 20 positioned between the ligamentum flavum and the spinal cord in accordance with an embodiment of the disclosure.

DETAILED DESCRIPTION

Figure 8:
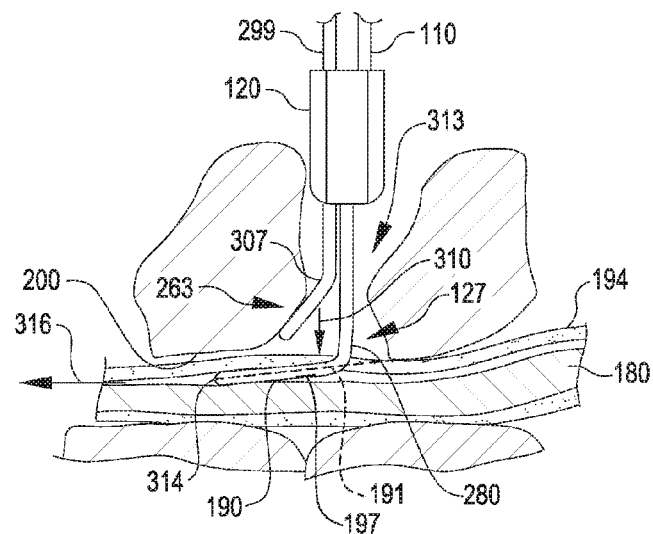

The following disclosure describes various embodiments in medical systems, instruments, devices, and associated methods of use. At least some embodiments include a visualization instrument that can be viewed to assist in a spinal procedure. Visualization techniques can be used to view at least a portion of a treatment instrument (e.g., a distal tip of a tissue removal instrument) and at least a portion of the visualization instrument to perform the procedure. Certain details are set forth in the following description and in FIGS. 1-26 to provide a thorough understanding of such embodiments of the disclosure. Other details describing well-known structures and systems often associated with, for example, visualization, treating the spine, spinal nerves (e.g., nerves in the spinal cord, nerves in nerve roots exiting the spinal cord, etc.), or decompression procedures are not set forth in the following description to avoid unnecessarily obscuring the description of various embodiments of the disclosure.

The terms "distal" and "proximal" within this description, unless otherwise specified, reference a relative position of the portions of a system, instruments, and/or associated delivery devices with reference to an operator and/or a location in the patient. For example, in referring to visualization instruments described herein, the term "proximal" can refer to a position closer to the operator, and the term "distal" can refer to a position that is more distant from the operator.

A. Overview

At least some visualization instruments disclosed herein can be used to identify features, such as targeted tissue and non-targeted tissue, and/or used as a point of reference to position other instruments and tools. In some embodiments, a visualization instrument can be positioned to protect the spinal cord and define a working space. A series of treatment instruments can be moved within the working space to crush, separate, cut, debulk, break, fracture, remove, or otherwise alter tissue at a treatment site. If the treatment instruments move towards the spinal cord, the visualization instrument can serve as a working barrier to inhibit or prevent injury and/or trauma to the spinal cord.

At least some embodiments are methods for treating a subject (e.g., a human subject). The methods include positioning a tissue protector of a visualization instrument in an epidural space. The tissue protector can be viewed via fluoroscopy to identify margins of the epidural space, dura, ligamentum flavum, nerve roots, and/or other tissue. The wide range of different types of fluoroscopy (e.g., anterior posterior imaging, lateral imaging, contralateral oblique imaging, etc.) can be used to view the visualization instrument, as well as treatment tools or delivery devices used to perform a procedure.

At least some embodiments are methods for performing a procedure on a subject and include positioning a distal portion of a visualization instrument in a vertebral column of the subject. Another instrument (e.g., a treatment instrument) can be positioned while viewing both the treatment instrument and a distal portion of the visualization instrument under, for example, fluoroscopy. A spinal decompression procedure can be performed using the treatment instrument. In one embodiment, the visualization instrument can be a radiopaque epidural catheter having a flexible elongated main body. In some procedures, the epidural catheter can be moved along the vertebral column through any number of vertebrae. In other embodiments, the visualization instrument is a catheter configured to be positioned within the dura sac or other suitable location. Such catheters can have a relatively low profile. An opening, if any, defined by, and laterally adjacent to, the distal portion can be smaller than a distal head or tool portion of the treatment instrument. As such, the distal head of the treatment instrument is prevented from contacting non-target tissue. In some embodiments, the visualization instrument includes an elongate radiopaque wire. The wire can extend from a distal end of the visualization instrument to a proximal end of the visualization instrument.

In some embodiments, a method for positioning an instrument in a subject comprises moving the tissue protector of the visualization instrument through a subject. The tissue protector can be moved from a delivery configuration to a deployed configuration to define a working space. A decompression procedure can be performed at the treatment site while viewing the deployed tissue protector. When using a treatment instrument at the working space, the treatment instrument and non-targeted tissue can be kept on opposite sides of the tissue protector.

In yet other embodiments, a method for performing a procedure on a subject includes positioning a tissue protector of a visualization instrument in an epidural space of a subject. A treatment instrument can be moved between a first vertebra and a second vertebra while the tissue protector remains in the epidural space and viewed via fluoroscopy. A physician can view both the treatment instrument and the tissue protector before, during, and after performing a procedure using the treatment instrument.

In some embodiments, a treatment system for treating spinal compression comprises a visualization instrument including a tissue protector configured to be positioned in an epidural space and viewed using a fluoroscopy. The treatment system can further include a treatment instrument configured to perform a decompression procedure at a treatment site while the tissue protector prevents access to the spinal cord. In some embodiments, the tissue protector can cover a posterior region of the spinal cord facing a treatment site.

B. Visualization Systems, Visualization Procedures, and Decompression Procedures FIG. 1 is a side view of a visualization system 100 in accordance with one embodiment of the disclosure. The visualization system 100 includes a visualization instrument 110 and a delivery device in the form of a cannula 120. The cannula 120 extends through a subject's skin 140, subcutaneous tissue 142, and a supraspinal ligament 150. The visualization instrument 110 extends through the cannula 120 and along a spinal or vertebral column 123.

FIG. 2 is a detailed side view of a portion of the visualization system 100. Vertebra 170, 174 are shown in cross section. FIG. 3 is a detailed superior anatomical view of a spinal canal 200. Referring to FIGS. 2 and 3 together, the visualization instrument 110 includes a distal portion 163 positioned between a ligamentum flavum 194 and a spinal cord 180. The spinal cord 180 is positioned between the ligamentum flavum 194 and a ligament 198 and extends from the brain to the bottom of the spine. Spinal nerves branch from the spinal cord 180, exit the spine, and extend to the parts of the body.

The distal portion 163 is viewable using, for example, fluoroscope, MR imaging, CT imaging, or other suitable imaging techniques. By viewing the distal portion 163, a physician can conveniently identify the location and/or margins of the spinal cord 180 and ligamentum flavum 194. The distal portion 163 can be moved to different positions to identify targeted or non-targeted tissue, which can include, without limitation, the ligamentum flavum 194, the spinal cord 180, the ligament 198, nerves branching from the spinal cord 180, vertebrae 170, 174, and other features or anatomical structures proximate to the spine. The distal portion 163 can include a tissue protector 190 (e.g., a section of the distal portion 163) configured to inhibit, limit, or substantially prevent damage and/or injury to the spinal cord 180 and can define a working space 127 (FIG. 2).

FIG. 4 is a flow chart illustrating a method 301 for visualizing and performing spinal nerve decompression in accordance with an embodiment of the disclosure. At stage 300, a delivery device can provide access to a treatment site. At stage 302, a visualization instrument can be positioned using fluoroscopy. At stage 304, one or more treatment instruments can be delivered to a working space defined, at least in part, by a tissue protector of the visualization instrument. At stage 305, a spinal procedure can be performed. The spinal procedure (including posterior lumbar decompression procedures) can involve altering tissue, implanting devices, or other procedures for treating various spine conditions. Tissue can be altered by cutting tissue, loosening tissue, crushing bone, or otherwise disrupting tissue at a treatment site. In some decompression procedures, tissue can be removed from one or more lateral recesses of a vertebra. In other decompression procedures, tissue can be removed from the spinal cord, vertebrae, or other site along the spine, as discussed in connection with FIGS. 8-19 and 22.

FIGS. 5-8 illustrate various stages of a procedure in accordance with one embodiment of the disclosure. Referring now to FIG. 5, the cannula 120 can be delivered using a posterior midline approach. An incision can be made in the supraspinal ligament 150 and the cannula 120 can be passed through the incision until it is inserted between spinous processes 240, 244. A distal end 252 of the cannula 120 can be positioned within an interspinous space 261. Delivery sheaths, delivery catheters, access ports, or other types of delivery devices can also be used to provide access to the treatment site. The distal portion 163 can be inserted into a proximal end 250 of the cannula 120, moved along a passageway of the cannula 120, and delivered out of the distal end 252. The distal portion 163 can be moved in the anterior direction through the interspinous space 261, through the ligamentum flavum, and into the epidural space (or other desired location).

FIG. 6 shows the visualization instrument 110 including the main body 280 and a proximal portion 269 positioned outside of the subject. The proximal portion 269 can include a steering assembly 270 used to steer the visualization instrument 110 by, for example, operating control elements 272, 274. One or more pull wires, pull rods, or other components can extend through the main body 280 and can be coupled to the distal end of the visualization instrument 110. The control elements 272, 274 can be levers, dials, or other elements that can be manipulated to bend, rotate, displace, or otherwise move the instrument 110. In other embodiments, the visualization instrument 110 may not have steering capability. A delivery device can be used to guide such visualization instruments to a desired site.

FIGS. 7 and 8 show a treatment instrument 299 that has been delivered through the cannula 120 and positioned at the working space 127. One or more markers (one marker 197 is shown in FIG. 8) can be used to identify the spinal cord 180 and can serve as a reference point to position the treatment instrument 299. However, markers can also be located on the exterior surface of the main body 280 and/or tissue protector 190, within the main body 280 and/or tissue protector 190, or at other suitable locations. Markers can include, without limitation, an array of radiopaque markers made of radiopaque materials, such as metals, radiopaque polymers, or the like. The radiopaque markers can be evenly or unevenly spaced apart along the length of the tissue protector 190. In other embodiments, the entire main body 280 and distal portion 193 can be made of radiopaque material. For example, the main body 280 and tissue protector 190 can be a flexible metal wire (e.g., an elongate radiopaque wire) or a bundle of flexible metal wires.

Referring to FIG. 8, a longitudinal axis 191 of the tissue protector 190 is oriented in the superior-inferior direction and is generally parallel to the long axis of the spinal cord 180. Additionally, the axis 191 can be generally perpendicular to the portion of the main body 280 extending in posterior-anterior direction. The ligamentum flavum 194 and spinal cord 180 can snugly hold the tissue protector 190 to help minimize movement of the instrument 110, even if the instrument 299 contacts the main body 280. An atraumatic tip 314 can be moved in the superior direction (indicate by arrow 316) to position most of the tissue protector 190 within the vertebral canal 200, but it can be located at other locations. In some embodiments, the tissue protector 190 can made of a compliant material (e.g., silicon, rubber, elastomers, etc.) to cushion tissue. In other embodiments, the tissue protector 190 can be made of a rigid or semi-rigid materials to distribute pressure to a large area of tissue.

FIG. 8 shows the instrument 299 having a working or distal portion 307 configured to break, cut, scrape, crush, or otherwise alter target tissue at the treatment site 263. The target tissue can include, without limitation, bone (e.g., lamina, bone of lateral recesses, facets, including inferior facets, etc.), bone spurs (e.g., bone spurs associated with osteoarthritis), tissue bulging from discs, tissue of thickened ligaments, spinal tumors, displaced tissue (e.g., tissue displaced by spinal injury), or other tissue that may cause or contribute to spinal nerve decompression. In procedures treating stenosis, the distal portion 307 can be used to remove tissue associated with central canal stenosis, lateral recess stenosis, or other types of stenosis.

If the distal portion 307 is moved in the anterior direction (indicated by arrow 310) the tissue protector 190 can physically block the distal portion 307. The distal portion 307 can also be inserted into the vertebral canal 200 without injuring or traumatizing the spinal cord 180. As a result, the instrument 299 can be safely moved throughout the working space 127. The shape and configuration of the tissue protector 190 can be selected based on the configuration of the distal portion 307. For example, the tissue protector 190 can be large enough to ensure that exposed regions, if any, of the spinal cord 180 (i.e., the regions of the spinal cord 180 accessible via the interspinous space 313) are smaller than the distal portion 307.

The treatment instrument 299 can be, without limitation, a surgical instrument (e.g., a scalpel), scraping instrument, cutting instrument, or other instrument or tool for altering tissue. U.S. Patent Application No. 61/755,392, filed on Jan. 22, 2013, discloses various types of surgical instruments that can be used in, or incorporated into, the systems and methods disclosed herein. Such instruments include, but are not limited to, debulker instruments, tissue removal instruments, cutting instruments, and debulker instruments and other systems, instruments, and devices disclosed in U.S. Application No. 61/755,329, which is incorporated by reference in its entirety.

To help position the distal portion 307, both the distal portion 307 and the tissue protector 190 can be viewed using, for example, fluoroscopy. The tissue protector 190 can serve as a reference point to help the physician identify critical areas of non-targeted tissue and/or assist in positioning of the distal portion 307. In some procedures, the tissue protector 190 can remain substantially stationary while the distal portion 307 is used to perform a procedure at the treatment site 263, although the tissue protector 190 can be repositioned any number of times during a treatment session.

After completing the procedure, the instrument 299 can be removed from the subject. The visualization instrument 110 and the cannula 120 can then be removed from the subject without injuring and/or traumatizing tissue.

Figure 9:
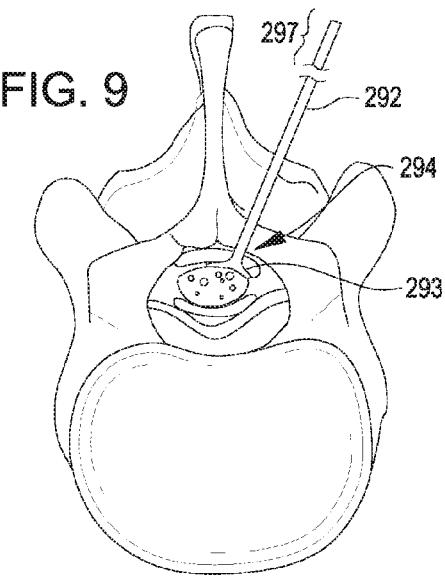
FIG. 9 is a superior anatomical view of a visualization instrument positioned using a transforamonal approach in accordance with an embodiment of the disclosure.
Figure 10:
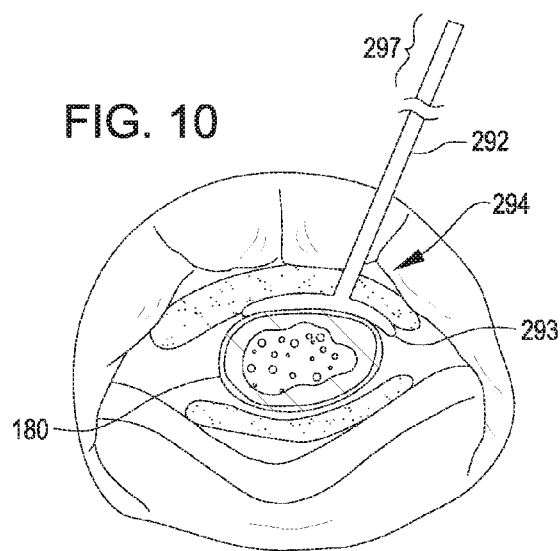
FIG. 10 is an enlarged view of the visualization instrument of FIG. 9 adjacent to the spinal cord in accordance with one embodiment of the disclosure.

FIGS. 9 and 10 show a visualization instrument 292 positioned using a transforaminal approach. The visualization instrument 292 can include a distal portion 294 with a tissue protector 293 extending laterally about the spinal cord 180 to provide a wide working space. An operator can grip the proximal portion 297 positioned outside of the subject to reposition the tissue protector 293. Treatment instruments or tools can be delivered using a transforaminal approach to perform decompression procedures at, for example, the lateral recesses. The tissue protector 293 can have a generally rectangular shape, partially cylindrical shape, or other shape or configuration suitable for overlaying the spinal cord 180.

Figure 11:
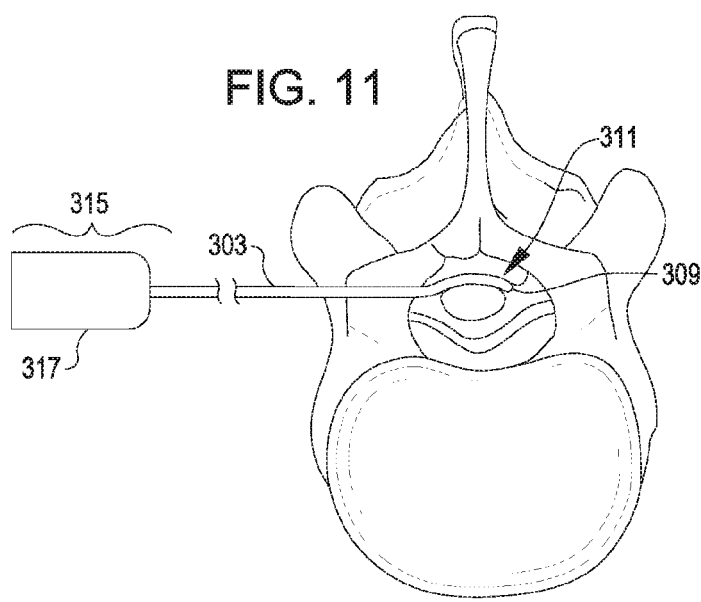
FIG. 11 is a superior anatomical view of a visualization instrument positioned using a lateral approach in accordance with an embodiment of the disclosure.
Figure 12:
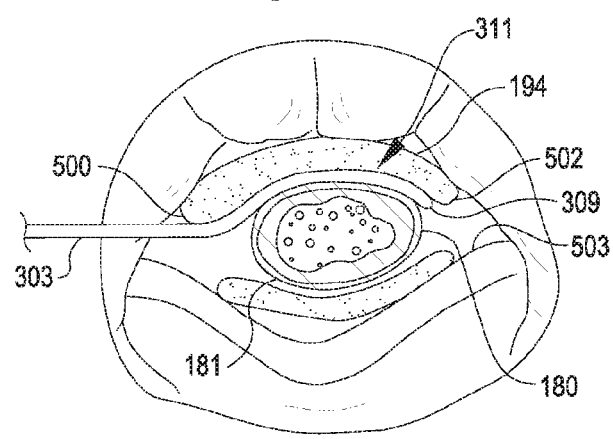
FIG. 12 is an enlarged view of the vertebral foramen of FIG. 11 with the visualization instrument positioned between the spinal cord and the ligamentum flavum.

Visualization instruments can be delivered using other access techniques. For example, FIGS. 11 and 12 show a visualization instrument 303 positioned using a lateral approach and having a distal portion 311 with a tissue protector 309 overlaying the posterior region of the dura sac 181. FIG. 12 shows the tissue protector 309 adjacent to opposing sides 500, 502 of the ligamentum flavum 194. In some embodiments, the tissue protector 309 wraps around most of the circumference of the spinal cord 180 to protect the dura sac 181 when performing decompression procedures at the lateral-most regions of the vertebral foramen 503. An operator can use a handle 317 (FIG. 11) at the proximal portion 315 (FIG. 11) to manually reposition the tissue protector 309.

Figure 13:
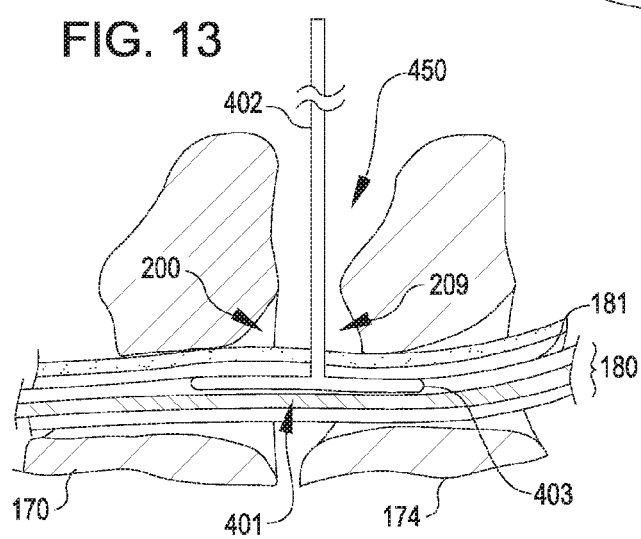
FIG. 13 is a side view of a distal portion of a visualization instrument positioned within a dura sac in accordance with an embodiment of the disclosure.
Figure 14:
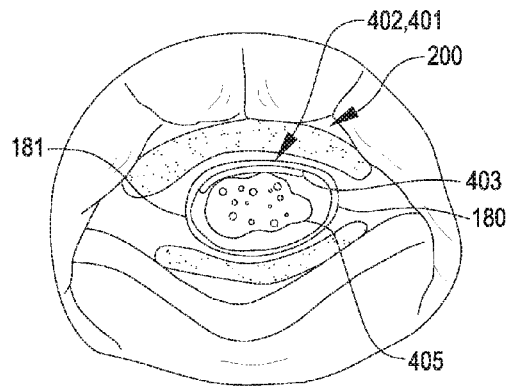
FIG. 14 is a superior anatomical view of the vertebral foramen of FIG. 13 in accordance with an embodiment of the disclosure.

FIGS. 13 and 14 show a visualization instrument 402 that includes a distal portion 401 with a tissue protector 403 positioned within dura sac 181. Referring to FIG. 13, the tissue protector 403 spans a gap 209 between the vertebra 170, 174. As such, the entire length of the spinal cord 180 positioned between the vertebra 170, 174 is protected. Other visualization instruments can also be positioned within the spinal cord 180. For example, the visualization instrument 110 of FIGS. 1 and 2 can be inserted into the dura and moved in the anterior or superior direction. To perform a myelogram, such instrument can have a port capable of delivering contrast media directly into the spinal cord 180.

Referring now to FIG. 14, the tissue protector 403 is positioned between the dura sac 181 and spinal nerves 405. If a treatment instrument or tool punctures the dura sac 181, the tissue protector 403 can shield the spinal nerves 405. Multiple visualization instruments can be used together in a single procedure. In one procedure, the visualization instrument 402 can be used to protect spinal nerves 405 while another visualization instrument, such as the visualization instrument 110 of FIGS. 1 and 2, protects the dura sac 181.

Figure 15:
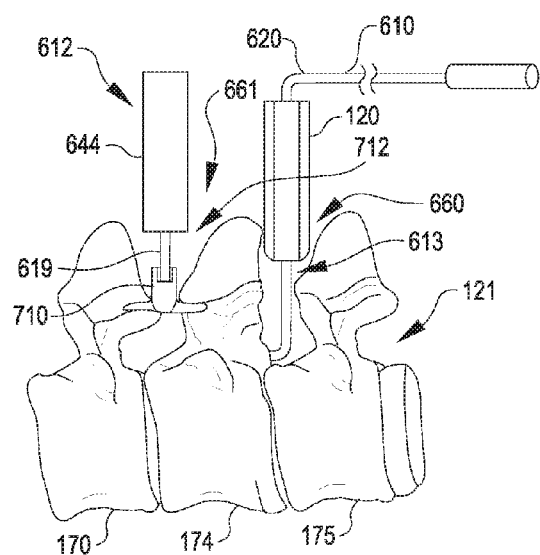
FIG. 15 is a side view of a visualization system and a treatment system positioned at different levels along a spine in accordance with an embodiment of the disclosure.
Figure 16:
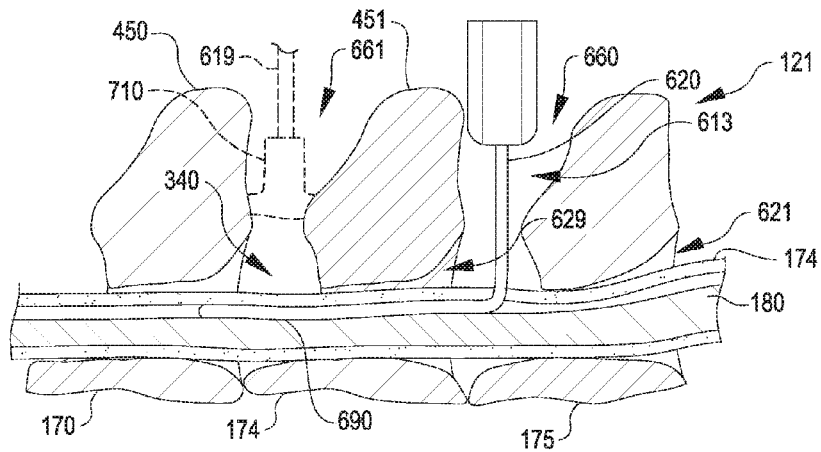
FIG. 16 is a side view of the visualization system and the treatment system of FIG. 15 with the spine shown in cross-section.

FIG. 15 is a side view of a visualization instrument 610 and a treatment system 612 in accordance with an embodiment of the disclosure. FIG. 16 is a detailed side view of portions of the visualization instrument 610 and treatment system 612. The spine 121 is shown in cross-section in FIG. 16. The visualization instrument 610 extends through an interspinous space 613 and its main body 620 extends through the vertebral canal 629 (FIG. 16). A tissue protector 690 can extend along the spinal canal 621 to a location superior to the treatment site. In FIG. 16, the treatment site is between the spinous processes 450, 451, so the tissue protector 690 can extend from a first level 660 to an adjacent level 661, thereby spanning a gap 340 (FIG. 16).

Referring again to FIG. 15, the treatment system 612 can include a delivery device in the form of a cannula 644, an instrument 619, and an implantable device 710. The implantable device 710 can be an interspinous spacer, fixation device, plate, or other type of spinal implant. One suitable such implantable device is the Superion® interspinous spacer from VertiFlex, Inc. or other similar device. The implantable device 710 can be implanted while imaging the device 710 and the tissue protector 690 and can be delivered via a midline approach, a transforaminal approach, an ipsilateral approach, or a lateral approach. The implantable device 710 can be deployed to engage, and couple to, the spinous processes 450, 451 to, for example, reduce or eliminate spinal compression, pain, or combinations thereof. Throughout the deployment process, the spinal cord 180 is protected by the tissue protector 190.

After implanting the device 710, the treatment system 612 can be removed from the subject. The visualization instrument 610 can be pulled proximally through the cannula 120 and removed from the subject. The visualization instrument 610 and treatment system 612 can be used to treat other locations along the spine.

FIG. 17 shows a visualization instrument 800 entering the spine at the lumbar region 810. A treatment instrument 820 can perform a procedure at the thoracic region 812 while a tissue protector 833 (shown in phantom) protects non-targeted tissue at the thoracic region 812. The visualization instrument 800 can be a catheter (e.g., a radiopaque epidural catheter or other instrument disclosed herein). FIG. 18 shows the visualization instrument 800 accessing the spine or vertebral column at the thoracic region 812 to protect non-targeted tissue at the lumbar region 810. FIG. 19 shows the visualization instrument 800 positioned at the sacral region 850 to perform a procedure at another level. Because the tissue protectors disclosed herein can be conveniently moved along the spine, the tissue protectors can be inserted at an access that is separated from the treatment site by one or more vertebrae. Accordingly, the access site can be at the cervical region, thoracic region, lumbar region, or sacral region to perform a procedure at treatment site at the cervical region, thoracic region, lumbar region, or sacral region.

FIG. 20 is a side view of a visualization instrument 900 that includes a distal portion 901, a proximal portion 903, and a main body 905. The distal portion 901 includes a tissue protector 902 in accordance with an embodiment of the disclosure. FIG. 21 is a plan view of the tissue protector 902 that includes protective arms 912 (individually 912a, 912b, 912c, 912d, 912e, 912f in FIG. 21) movable from a delivery configuration 917 (shown in phantom line in FIG. 20) to the deployed configuration 919. To deliver the tissue protector 902, the arms 912 can be in the delivery configuration 917 for delivery through a cannula or other delivery device. As the tissue protector 902 exits the cannula, the arms 912 to move from the delivery configuration to the deployed configuration, as indicated by arrow 924, 926. In some embodiments, the arms 912 are biased outwardly and can self-deploy. In other embodiments, the arms 912 can be deployed using one or more balloons, pull rods, pull wires, or other component for providing controlled movement of the arms 912.

Referring to FIG. 21, the arms 912 can be generally evenly spaced apart from one another and made of metal, plastic, or other material capable of withstanding contact with a treatment instrument so as protect adjacent tissue. In some embodiments, a protective or shielding member 920 (shown in phantom line) can be carried by the arms 912 and can include, without limitation, a mesh, a net, a sheet (single layer or multilayer layer sheet), drapable fabric, a plate, or other protective barrier (i.e., a barrier for preventing injury or trauma to tissue) that can assume different configurations by expanding, unfurling, or the like. The protective member 920 can have a wide range of shapes and configurations, including a generally circular shape, spherical shape, rectangular shape, or the like.

FIG. 22 shows the tissue protector 902 in the deployed configuration. Tips 930 of the arms 912 can be positioned within vertebral canals 200, 204 to protect the entire length of the spinal cord 180 exposed by the interspinous space 911. In some embodiments, the entire portion of the spinal cord 180 accessible via the interspinous space 911 is covered by the protective member 920 to prevent puncturing of the dura sac 181, while the arms 912 can help withstand significant forces from treatment instruments. Accordingly, the arms 912 and protective member 920 can work together to provide enhanced protection.

Figure 23:
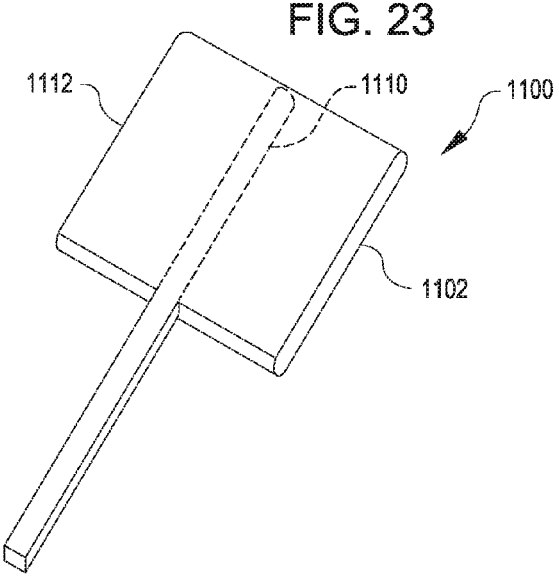
FIG. 23 is an isometric view of a visualization instrument in accordance with an embodiment of the disclosure.

FIG. 23 is an isometric view of a visualization instrument 1100 including a tissue protector 1102 in accordance with another embodiment of the disclosure. The tissue protector 1102 is movable from a delivery configuration 1110 (shown in phantom line) to the deployed configuration 1112. The tissue protector 1102 can include an inflatable member (e.g., a single chamber balloon, a multi-chamber balloon) that can be inflated with a fluid to provide cushion to further inhibit or prevent tissue trauma and/or injury. Such inflatable members can be made of a highly compliant material, including, without limitation, silicon, rubber, elastomers, or the like. One or more markers can be positioned along the exterior surface or within the tissue protector 1102. The inflation fluid can be visualization media (e.g., contrast media) in the form of a flowable radiopaque substance (e.g., a radio contrast agent, barium sulfate solution, or the like) or other viewable substance. Non-ionic contrast media can be used if the tissue protector 1102 is positioned within the dura sac. As a result, the inflation fluid can provide both cushioning and visualization functionality.

Figure 24:
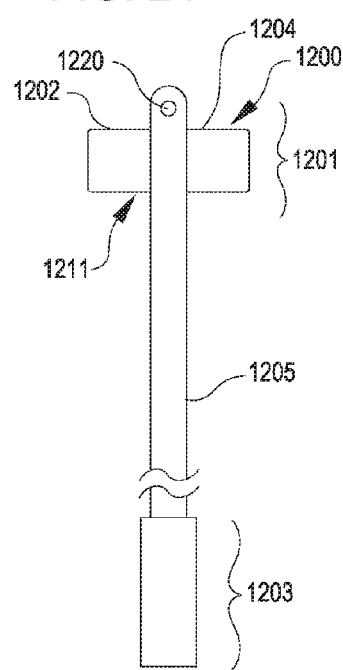
FIG. 24 is a plan view of a visualization instrument capable of delivering contrast media in accordance with an embodiment of the disclosure.

FIG. 24 is an elevational view of a visualization instrument 1200 that includes a distal portion 1201, a proximal portion 1203, and a main body 1205 therebetween. The distal portion 1201 includes a tissue protector 1211 having deployable elements 1204, 1204 movable from a delivery configuration inside the body 1205 to the illustrated deployed configuration. Visualization media can be delivered out of a port 1220 for additional imaging. To perform an epidurogram, the visualization media can be delivered out of the port 1220 when the tissue protector 1211 is positioned in the epidural space. The members 1202, 1204 can be deployed before, during, or after delivery of the visualization media. Other visualization instruments disclosed herein can also include one or more ports for delivering media.

Figure 25:
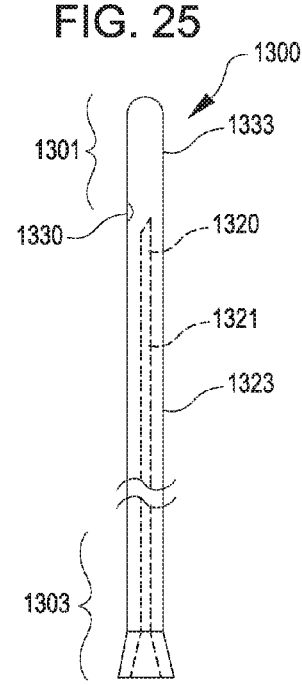
FIG. 25 is a plan view of a visualization instrument with the deployable media delivery element in accordance with an embodiment of the disclosure.
Figure 26:
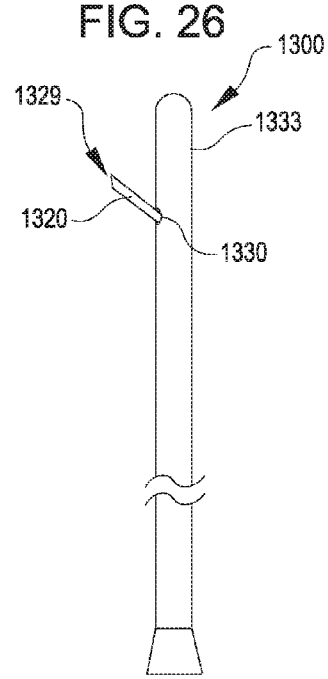
FIG. 26 is a plan view of the delivery element of FIG. 25 in a deployed position.

FIG. 25 is a side elevational view of a visualization instrument 1300 in accordance with an embodiment of the disclosure. FIG. 26 is a side view of the visualization instrument 1300. Referring to FIG. 25, the visualization instrument 1300 includes a distal portion 1301, a proximal portion 1303, a main body 1305, and a media delivery element 1320 in an undeployed position. In some embodiments, the media delivery element 1320 can be housed within a lumen 1321. Referring to FIG. 26, the delivery element 1320 can be moved out of an aperture 1330 to deliver media.

In myelography procedures, a tissue protector 1333 can moved along the epidural space adjacent to the dura. The delivery element 1302 can be moved out of the aperture 1330, which faces the dura, to puncture the dura sac. After an end 1329 is within the dura, visualization media (e.g., a non-ionic contrast media) can be delivered directly into the spinal fluid surrounding the spinal cord. The delivery element 1320 can be positioned under fluoroscopic guidance to ensure that spinal nerves are not damaged or injured. After delivering the media, the delivery element 1302 can be drawn back into the main body 1323. As such, the media can be kept outside of the epidural space and localized within the dura. Myelography can provide detailed images (i.e., myelograms) of the spinal cord, thecal sac, nerve tissue (including nerve roots), or other features of interest. Additionally, myelography procedures can provide enhanced viewing of non-targeted structures (e.g., dura), and nerve roots compared to epidurography procedures. For example, visualization media of a myelography procedure may travel (e.g., via controlled leakage) to nerve roots to visualize the nerve roots when removing bone of the neural foramen. In some embodiments, myelography visualization media can be used to verify decompression of the spinal cord because the dura can move outwardly to confirm that the pressure applied to the spinal cord is decreased or eliminated. If the dura is damaged (e.g., tears, leaks, or the like), myelography visualization media can escape out of the damaged region of the dura. A physician can view the leakage to confirm that the dura has been damaged, as well as identifying the location of the damage. The physician can then repair the dura or otherwise alter the surgical procedure. Accordingly, myelography visualization media can be used to provide useful real-time feedback. Other visualization instruments disclosed herein can have delivery elements similar to the delivery element 1302 discussed in connection with FIGS. 25 and 26 in order to deliver contrast media (or other media) into tissue. For example, the tissue protector 190 of FIG. 2 can have a deployable delivery element.

Although many embodiments discussed herein are discussed in the context of fluoroscopy, other visualization techniques can be used to view treatment instruments and/or visualization instruments to identify targeted features, treatment sites, and/or non-targeted features. Treatment instruments and/or visualization instruments can be viewed when altering tissue and/or delivering a spinal device, such as a spinal implant, a spacer device, prosthetics disk, or the like. In certain procedures, visualization instruments disclosed herein can be used to identify margins of the epidural space, dura, ligamentum flavum, and/or nerve roots relative to the lamina and interlaminar space, as well as the features of instruments.

The visualization instruments disclosed herein can be located at other locations to protect other non-target tissue. Other embodiments can include tissue protectors specifically designed to protect portions of the vertebrae, nerve roots, or other structures near the spine. Additionally, multiple visualization instruments can cooperate to simultaneously protect tissue while also serving as reference points under visualization.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. For example, features from various instruments can be combined with features and methods disclosed in U.S. Pat. Nos. 8,012,207; 8,123,807; 8,152,837, and U.S. application Ser. No. 12/217, 662 (U.S. Publication No. 2008/0287997) which are incorporated by reference in their entireties. U.S. Provisional Application Nos. 61/639,828, 61/745,470, and 61/755,329, which are hereby incorporated by reference herein and made a part of this application. A wide range of treatment instruments can be used to address a wide range of symptoms, conditions, and/or diseases, including, without limitation, spinal nerve compression (e.g., spinal cord compression, spinal nerve root compression, or the like), spinal disk herniation, osteoporosis, stenosis, or other diseases or conditions. In one embodiment, the system 100 is used to perform a spinal cord decompression procedure, which can include removing bone from one or more vertebrae, separating the ligamentum flavum from one or more vertebrae, cutting or debulking the ligamentum flavum, and/or removing loose tissue.

Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for performing a procedure on a subject, comprising:
   positioning a distal portion of a visualization instrument in a vertebral column of the subject such that the visualization instrument extends through a vertebral canal of a first vertebra, a vertebral canal of a second vertebra, and a vertebral canal of a third vertebra of the vertebral column;
   moving a treatment instrument between the first vertebra and the second vertebra of the vertebral column while viewing the distal portion of the visualization instrument positioned in the vertebral column using fluoroscopy;
   performing a first spinal decompression procedure at a first level along the vertebral column using the treatment instrument positioned between the first and second vertebrae while the visualization instrument extends between the first and second vertebrae; and
   performing a second spinal decompression procedure at a second level along the vertebral column while the visualization instrument extends between the third vertebra and another vertebra.

2. The method of claim 1 wherein positioning the distal portion of the visualization instrument includes moving the distal portion into an epidural space adjacent to the first vertebra or the second vertebra.

3. The method of claim 1 wherein positioning the distal portion of the visualization instrument includes moving a distal tip of the distal portion through the vertebral canal of the first vertebra, the vertebral canal of the second vertebra, and the vertebral canal of the third vertebra while a proximal portion of the visualization instrument is positioned outside of the subject.

4. The method of claim 1 wherein positioning the distal portion of the visualization instrument includes positioning the distal portion relative to the vertebral column to cover an exposed portion of the subject's spinal cord.

5. The method of claim 1 wherein the distal portion includes at least one radiopaque marker.

6. The method of claim 5 wherein positioning the distal portion includes positioning the radiopaque marker between a dura sac of the subject and an interspinous space between a spinous process of the first vertebra and a spinous process of the second vertebra.

7. The method of claim 1 wherein positioning the distal portion comprises:
   positioning a distal end of a cannula in the subject; and
   moving the distal portion through the cannula and into an epidural space of the subject.

8. The method of claim 7 wherein moving the treatment instrument comprises moving a distal end of the treatment instrument through the cannula.

9. The method of claim 1, further comprising delivering an interspinous spacer to an interspinous space between the first vertebra and the second vertebra while viewing the distal portion.

10. The method of claim 1, wherein performing the first spinal decompression procedure includes removing bone from the vertebral column, separating a portion of a ligamentum flavum from one of the first and second vertebrae, and/or removing a portion of the ligamentum flavum of the subject.

11. The method of claim 10, further comprising removing the visualization instrument from the subject after performing the first spinal decompression procedure.

12. The method of claim 1 wherein the distal portion comprises an inflatable member movable between a delivery configuration and a deployed configuration.

13. The method of claim 1 wherein the visualization instrument includes an elongate radiopaque wire.

14. The method of claim 1, further comprising:
    moving a cannula through the subject's supraspinal ligament;
    moving the visualization instrument through the cannula extending through the supraspinal ligament to position the distal portion through the vertebral canal of the second vertebrae such that the distal portion extends through the vertebral canals of the first and second vertebrae; and
    delivering media from the visualization instrument to perform an epidurogram or a myelogram.

15. The method of claim 1 wherein the visualization instrument extends across an entire length of the subject's spinal cord between the first and third vertebrae while performing the first and second spinal decompression procedures.

16. A method for treating a subject, comprising:
    moving a cannula through the subject's supraspinal ligament;
    moving a tissue protector of a visualization instrument through the cannula extending through the supraspinal ligament and into the subject;
    moving the tissue protector through vertebral canals of three vertebrae to define a first working space and a second working space, the first working space including a first treatment site, the second working space including a second treatment site, wherein the first and second working spaces are between different vertebrae;
    performing at least a portion of a first decompression procedure at the first treatment site while viewing the tissue protector positioned in the vertebral canals; and
    performing at least a portion of a second decompression procedure at the second treatment site while viewing the tissue protector positioned in the vertebral canals.

17. The method of claim 16 wherein the tissue protector physically blocks movement of a treatment instrument towards the dura sac while performing at least one of the first or second decompression procedures.

18. The method of claim 16 wherein the tissue protector comprises a balloon, a net, a sheet, or a drapable fabric.

19. A method for performing a procedure on a subject, comprising:
    moving a tissue protector of a visualization instrument into an end of a first vertebral canal of a first vertebra, through the first vertebral canal, and out another end of the first vertebral canal;

moving the tissue protector into an end of a second vertebral canal of a second vertebra, through the second vertebral canal, and out another end of the second vertebral canal;

moving the tissue protector into an end of a third vertebral canal of a third vertebra, through the third vertebral canal, and out another end of the third vertebral canal;

viewing the tissue protector positioned in the subject's epidural space using fluoroscopy;

performing a first decompression procedure using one or more first treatment instruments positioned between the first vertebra and the second vertebra; and performing a second decompression procedure using one or more second treatment instruments positioned between the third vertebra and another vertebra through which the visualization instrument extends.

20. The method of claim 19, further comprising positioning a first portion of the tissue protector within the first vertebral canal of the first vertebra and a second portion of the tissue protector within the second vertebral canal of the second vertebra.

* * * * *